United States Patent [19]
Bohley

[11] Patent Number: 5,250,045
[45] Date of Patent: Oct. 5, 1993

[54] OPTICAL FIBER CATHETER WITH SPACED OPTICAL FIBER

[75] Inventor: Thomas K. Bohley, Colorado Springs, Colo.

[73] Assignee: The Spectranetics Corporation, Colorado Springs, Colo.

[21] Appl. No.: 713,457

[22] Filed: Jun. 11, 1991

[51] Int. Cl.⁵ .................................... A61B 17/36
[52] U.S. Cl. .................................................. 606/7
[58] Field of Search .................... 606/2, 7, 10–16, 606/17; 385/115, 116, 117

[56] References Cited

U.S. PATENT DOCUMENTS

| | | | |
|---|---|---|---|
| 3,279,902 | 10/1966 | Gardner | 385/115 |
| 3,653,739 | 4/1972 | Strack | 385/115 |
| 4,207,874 | 6/1980 | Choy . | |
| 4,252,408 | 2/1981 | Parsons et al. | 385/115 X |
| 4,547,040 | 10/1985 | Yamamoto et al. | 385/115 X |
| 4,587,972 | 5/1986 | Morantte, Jr. . | |
| 4,615,583 | 10/1986 | Tsuno et al. | 385/116 X |
| 4,622,972 | 11/1986 | Giebeler, Jr. . | |
| 4,740,047 | 4/1988 | Abe et al. | 606/2 X |
| 4,768,858 | 9/1988 | Hossein | 606/7 X |
| 4,790,310 | 12/1988 | Ginsburg et al. . | |
| 4,819,632 | 4/1989 | Davies | 606/7 |
| 4,832,023 | 5/1989 | Murphy-Chutorian et al. . | |
| 4,834,093 | 5/1989 | Littleford et al. . | |
| 4,844,062 | 7/1989 | Wells . | |
| 4,848,336 | 7/1989 | Fox et al. . | |
| 4,905,689 | 3/1990 | Stack et al. . | |
| 4,913,142 | 4/1990 | Kittrell et al. . | |
| 4,917,084 | 4/1990 | Sinofsky . | |
| 4,934,340 | 6/1990 | Ebling et al. . | |
| 4,963,142 | 10/1990 | Loertscher | 606/14 |
| 4,984,859 | 1/1991 | Fujigaki et al. | 385/115 X |

Primary Examiner—Peter A. Aschenbrenner
Attorney, Agent, or Firm—Cushman, Darby & Cushman

[57] ABSTRACT

A laser catheter contains groups of optical fibers, each group forming a spiral pattern or radially straight lines, extending from near the inner wall of the laser catheter to the outer wall. The laser catheter is rotated about its longitudinal axis to ablate a target.

13 Claims, 4 Drawing Sheets

OPTICAL FIBER CATHETER WITH SPACED OPTICAL FIBER

BACKGROUND OF THE INVENTION

1. Field of the Invention

The present invention relates to an optical fiber catheter, and more particularly to as arrangement of optical fibers within an optical fiber catheter, near its distal end.

2. Description of Related Art

Many teachings exist in the art for using optical energy delivered through a fiberoptic catheter assembly to ablate obstructions within blood vessels. One such teaching is revealed in the U.S. Pat. No. 4,844,062, to Wells. Wells uses a laser catheter to ablate an area larger than the cross-sectional area of a single fiber or fiber bundle inside the catheter. This is done by rotating the fiber or fiber bundle, which covers the center of the catheter, around a guide wire that is eccentric inside the catheter. Since only a single fiber or bundle is employed, only a small area, albeit larger than the cross-sectional area of the fiber or bundle, can be ablated.

Kitrell et al., in his U.S. Pat. No. 4,913,142 discloses a laser cathether containing optical fibers for carrying laser light. A shield is mounted on its distal end for displacing intravascular blood and preventing the fiber from the blood's corrosive contents.

Other examples include U.S. Pat. Nos. 4,207,874, to Choy, 4,587,972 to Morantte, Jr. 4,622,972 to Giebeler, Jr., 4,790,310 to Ginsburg et al. 4,832,023 to Murphy-Chutorian et al. and so on.

However, none of the above-mentioned patents address the issue of providing a highly flexible optical fiber catheter for ablating a large target area without requiring an extremely powerful laser. When the desired ablation area is large, conventional thinking requires that an optical fiber catheter with a correspondingly large distal diameter be used. For such a catheter to ablate the area uniformly, a large number of optical fibers must be packed within the outer lumen of the catheter (See FIG. 1). For example, constructing a catheter of 2 mm in diameter or larger requires 80 or more 100 micron fibers. Furthermore, the cross-sectional area of a laser catheter, which varies directly with the required number of optical fibers to fill it, increases in proportion to the square of its diameter. The number of required optical fibers for packing the catheter can become prohibitively great as the required diameter increases. Increasing the number of fibers decreases the flexibility of the catheter.

In addition, as the number of optical fibers becomes large, more power must be delivered by the energy source that drives the fibers. In the above example with 2 mm catheter, a laser must deliver more than 100 mJ.

Clearly, construction and operation of catheters for ablating a large target can become difficult and expensive.

SUMMARY OF THE INVENTION

It is an object of the present invention to provide a simple and flexible fiber optic catheter structure for ablating a large area, the fiber optic catheter housing few optical fibers within.

It is a further object of the present invention to provide a large-area ablation catheter requiring less optical optic energy than conventional large-area ablation catheters.

It is also an object of the present invention to provide a method for constructing such catheters.

In the present invention, optical fibers near the distal end of a fiber optic catheter may be fixed so that the optical fibers are spaced apart from each other. That is, the optical fibers may be organized in groups. Within each group, adjacent fibers have ends which are radially contiguous to each other. However, the groups of fibers are spaced apart from each other. During an operation such as laser angioplasty, the catheter may be rotated to uniformly ablate target tissues.

The ends of the optical fibers in the catheter may be arranged in a spiral pattern. In such embodiment, the fiber optic catheter houses rows of optical fiber ends, and each row extends spirally from near the inner wall of the fiber optic catheter to its outer wall. To ablate a given target, optional energy is introduced into the optical fibers while the fiber optic catheter is rotated about its longitudinal axis.

Alternatively, the rows of the ends of optical fibers may extend straight, radially outward from the inner wall of the fiber optic catheter to the outer wall. To ablate a given area, the structure is rotated during the firing of an energy source such as a laser.

The ends of optical fibers may be arranged in patterns other than spirals or radially straight lines.

To ablate tissue, each optical fiber must emit optical energy at a level above a minimum fluence level. Because the fiber optic catheter of the present invention houses fewer optical fibers than conventional large-area catheters, the energy source to which the catheter is connected can output a lower total energy per pulse, yet maintain the same minimum fluence per optical fiber than with conventional catheters and ablate tissue over the same area. Furthermore, the reduction in the total energy per pulse delivered to the patient reduces the possibility of coronary trauma, such as coronary spasm, during ablations within coronary arteries.

Also, the catheter of the present invention retains more flexibility than conventional designs because the present invention contains fewer optical fibers.

BRIEF DESCRIPTION OF THE DRAWINGS

These and other objects and advantages of this invention will become more apparent and more readily appreciated from the following detailed description of the presently preferred exemplary embodiments of the invention, taken in conjunction with the accompanying drawings, of which.

DETAILED DESCRIPTION OF THE PRESENTLY PREFERRED EXEMPLARY EMBODIMENTS

Figure 1:
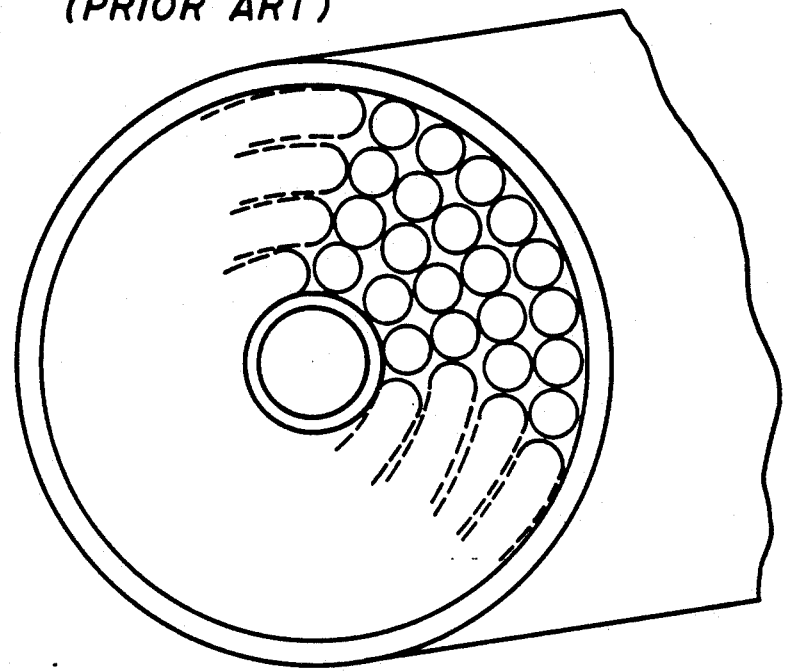
FIG. 1 shows a perspective view of an end of a prior art catheter.
Figure 2:
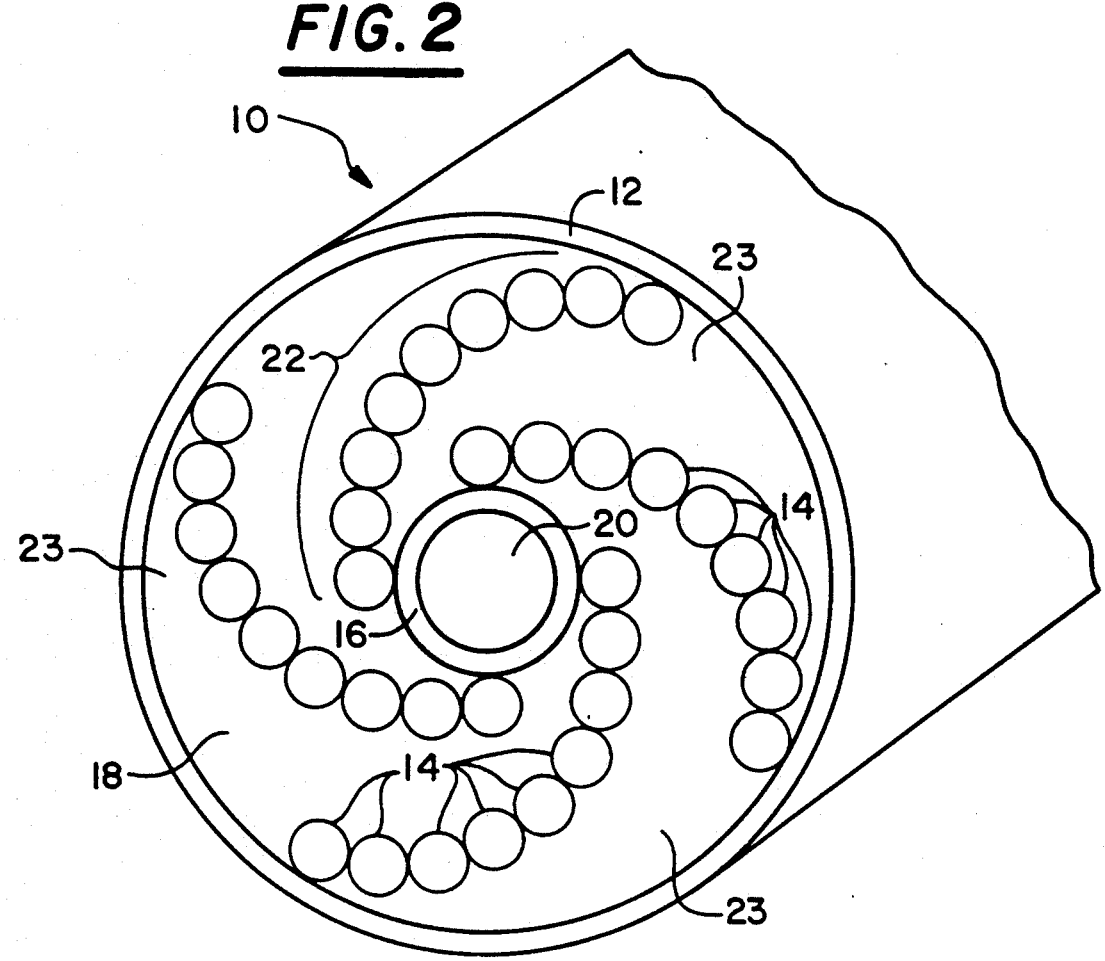
FIG. 2 shows a perspective view of an end of a first embodiment of the present invention.

The first embodiment of the present invention, shown in FIG. 2, includes outer wall 12, optical fibers 14, and inner wall 16. Inner wall 16 and outer wall 12 define outer lumen 18, and inner wall 16 encloses inner lumen 20. A guidewire may be inserted through inner lumen 20.

The distal ends of optical fibers 14 are arranged in groups 22. Within each group 22, the ends of individual optical fibers 14 are positioned in a spiral pattern and the ends are fixed with epoxy 23. Even though FIG. 2 shows only four groups 22, catheter 10 may house more or less groups within outer lumen 18.

It is noted that the arrangement of optical fibers 14 are as shown only at the distal end of catheter 10. The orientation of optical fibers 14 through the remainder of catheter 10 may be random, and they do not need to be affixed in a restricting position.

As an example, the diameter of each of optical fibers 14 may be approximately 100 microns, and the outer diameter of catheter 10 may be approximately 2 mm. The diameter of inner lumen 20 may be about 0.5-0.6 mm.

The present invention may be used to ablate obstructions within a blood vessel as follows. First, the proximal end of fiberoptic catheter 10 is connected to an energy source and the distal end of catheter 10 is placed in a correct location using a guide wire in a conventional manner. Next, the distal end of a fiber optic catheter 10 is rotated gradually as optical fibers 14 emit energy at a target. Thus, a target object may be ablated in a manner safe to the patient. The catheter is rotated until an entire area equivalent to the cross-sectional area of the catheter is ablated. Obviously, as the number of groups of fibers 22 increases, the necessary angle of rotation decreases. With four equiangularly positioned groups 22 as in FIG. 2, the necessary angle of rotation is 90°. As the number of groups of fibers 22 increases, the advantages of the present invention diminish.

Figure 3:
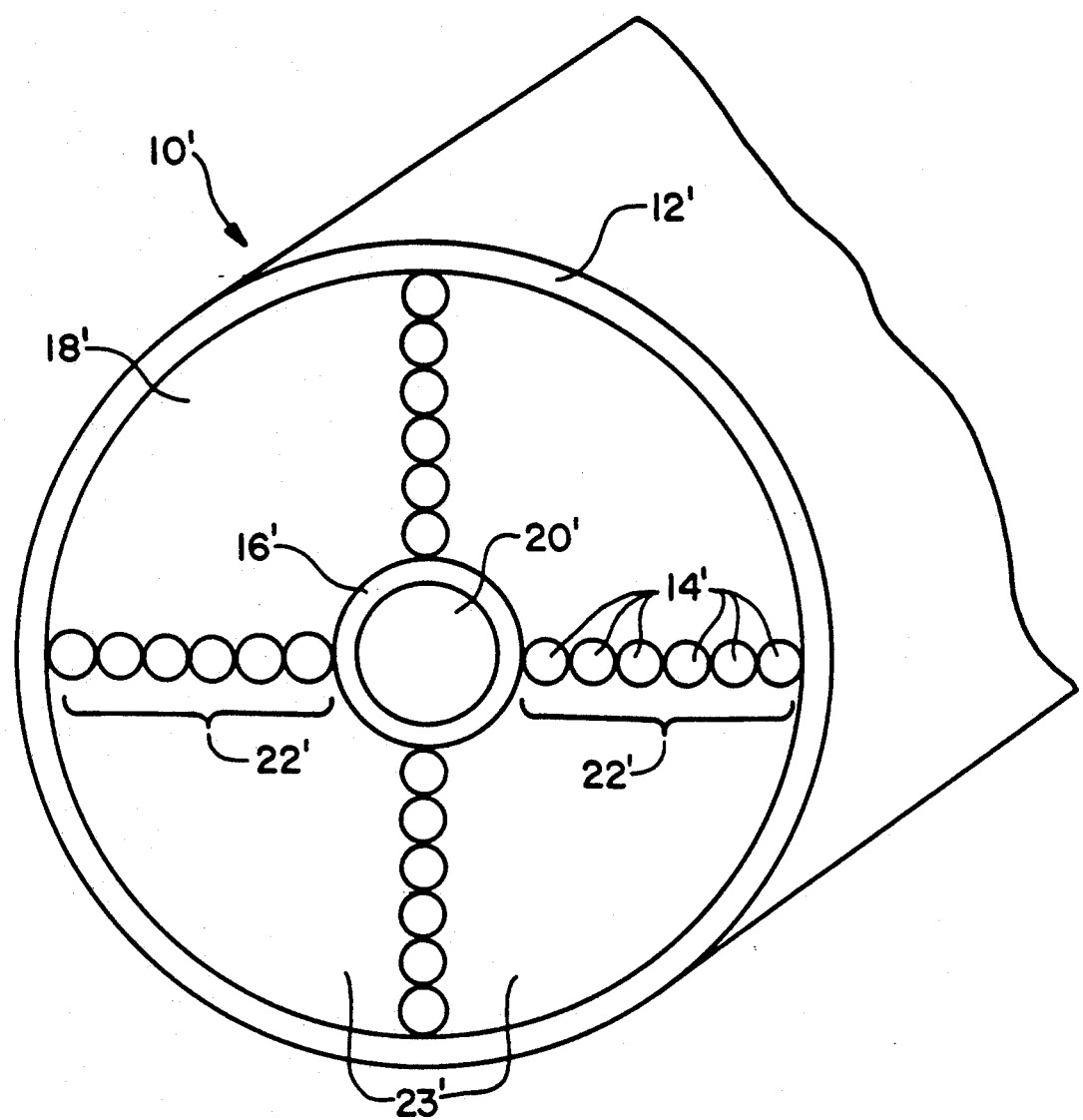
FIG. 3 shows a perspective view of an end of a second embodiment of the present invention.

FIG. 3 shows a second embodiment of the present invention, again near its distal end. The parts corresponding to those of the first embodiment have been labelled with the same reference numerals, but with each numeral primed.

The primary difference between the first embodiment and the second embodiment is in the arrangement of group 22, 22' of optical fibers 14, 14'. In the first embodiment, the distal ends of the fibers in each group 22 are fixed in a spiral pattern. In the second embodiment, the distal ends of the fibers in each group 22' extend radially straight from inner lumen 20' to outer wall 12'.

Figure 4:
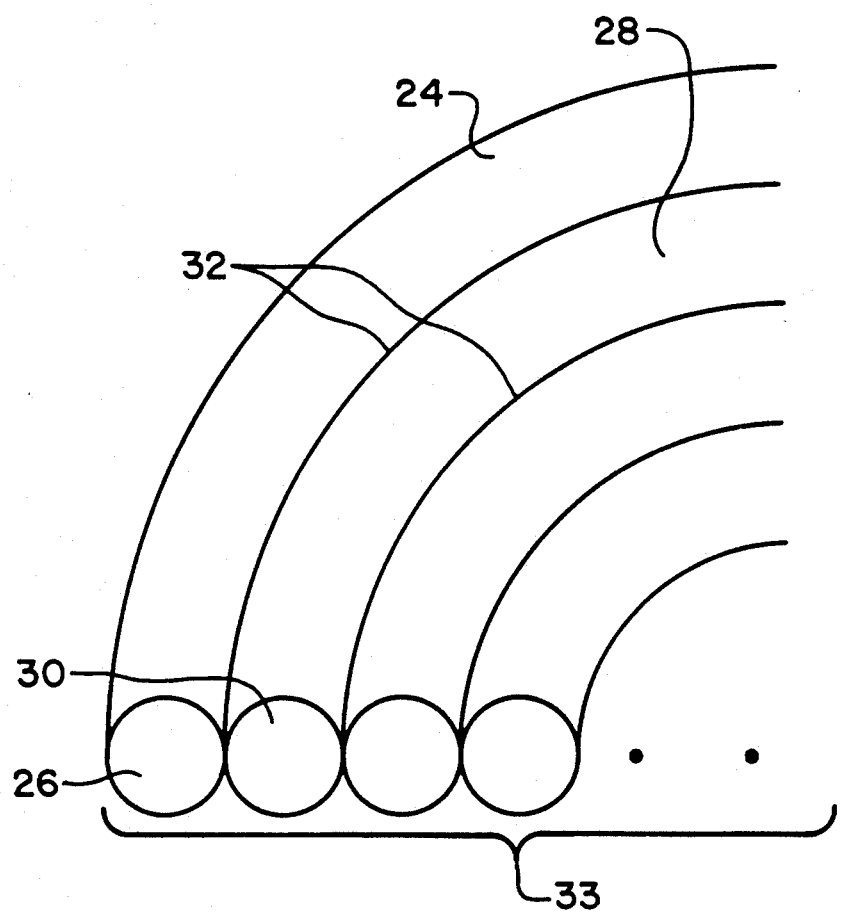
FIG. 4 illustrates areas traced by a row of energy beams output from optical fibers of the first embodiment.
Figure 5:
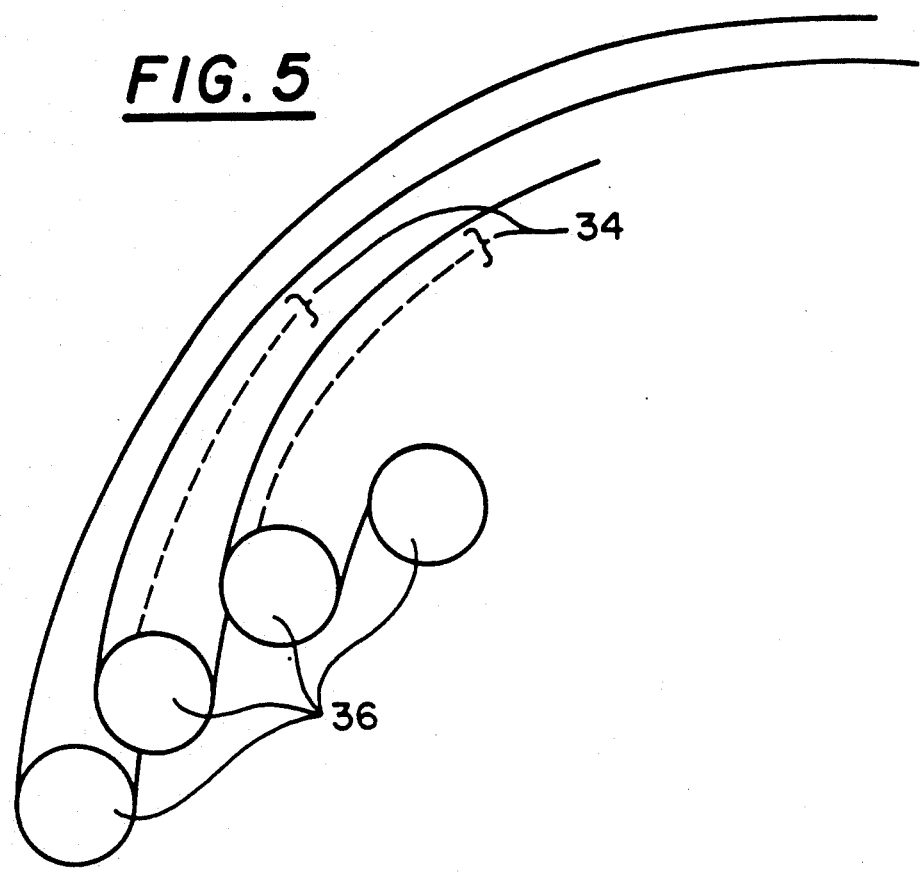
FIG. 5 illustrates areas traced by a row of energy beams output from optical fibers of the first embodiment.

The size and operation of the second embodiment are similar to that of the first embodiment, and such description is not repeated. It may be noted that in the second embodiment, as catheter 10' rotates, area 24 (FIG. 4) traced by outermost beam 26 (from one of fibers 14') does not overlap with area 28 traced by beam 30. Thus, there are regions 32, between areas swept by adjacent beams, that are exposed to less intense radiation. In the first embodiment, the spiral pattern within groups 22 allows for overlaps 34 between areas swept by adjacent beams 36 (FIG. 5), thus ensuring that the entire target area will be exposed to beams 36 in a relatively uniform manner.

Figure 6:
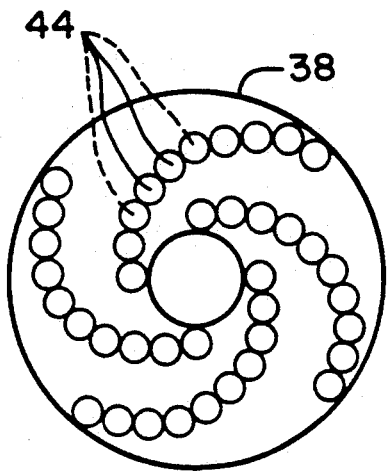
FIG. 6 and 7 show front elevational views of templates used in constructing the first and the second embodiments of the present invention.

The first embodiment may be constructed as follows. A template 38 (FIG. 6) with holes 42 may be placed at the distal end of catheter 10. Holes 42 form spiral patterns, and optical fibers 14 are passed through (not shown) holes 42 of template 38. Next, template 38 is positioned concentric with catheter 10 and while epoxy is applied to outer lumen 18 at the distal end to fix the fiber ends. Later when epoxy 23 solidifies, template 38 may be removed or cut away and the end of catheter 10 polished. Alternatively, template 38 may be positioned within catheter 10 while the epoxy is poured and then dried, so that template 38 remains in catheter 10.

Figure 7:
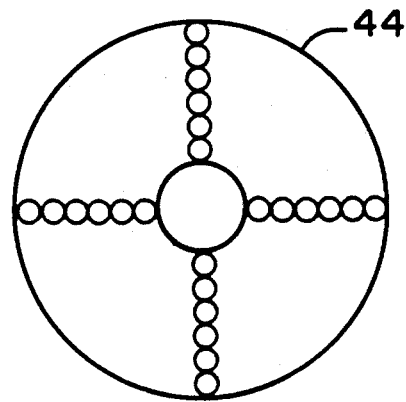

It is noted that, to construct the second embodiment, the above-described procedure may be applied to template 44 (FIG. 7).

As mentioned above, fiber optic catheters of the present invention contain few optical fibers. This permits inexpensive construction of large fiber optic catheters. Furthermore, required power for the driving optical energy source is also less, because fewer optical fibers 14 need to be energized. In the present invention, the danger of inducing coronary trauma is reduced because the present invention does not supply as much power to the target areas. Also, the present invention retains flexibility, because few optical fibers 14 are packed within catheter 10.

Although only a few exemplary embodiments of this invention have been described in detail above, those skilled in the art will readily appreciate that many modifications are possible in the preferred embodiments without materially departing from the novel teachings and advantages of this invention. For example, the present embodiments showed only four groups of optical fibers; however, if desired, more or fewer groups of optical fibers may be used. Accordingly all such modifications are intended to be included within the scope of this invention as defined by the following claims.

What is claimed is:

1. A fiber optic catheter comprising:
   an outer cylindrical wall;
   an inner cylindrical wall within and separated from said outer wall, said inner cylindrical wall defining an inner lumen therewithin; and
   a plurality of spaced groups of optical fibers disposed between said inner wall and said outer wall, each group of optical fibers comprising a plurality of optical fibers, each having a cross-sectional area, a sum of the cross-sectional areas of all of said optical fibers at a distal end of said catheter being substantially less than a cross-sectional area of said catheter between said outer wall and said inner wall at said distal end, said fibers of each spaced group being arranged at said distal end to sweep an area at the extreme distal end of said catheter over an entire radial length from said inner wall to said outer wall when said catheter is rotated about said inner lumen.

2. A fiber optic catheter as in claim 1 or 2, wherein said distal ends of said optical fibers in each said group area arranged along a radius of said catheter and between said inner wall and said outer wall.

3. A fiber optic catheter as in claim 1 or 2, wherein said distal ends of said optical fibers in each said group are arranged spirally from said inner wall to said outer wall.

4. A fiber optic catheter as in claim 1 or 2 further comprising means for holding said distal ends of said optical fibers in a fixed pattern.

5. A fiber optic catheter as in claim 4, wherein said holding means comprises epoxy.

6. A fiber optic catheter comprising:
an outer cylindrical wall;
an inner cylindrical wall;
at least one group of a plurality of optical fibers disposed between said inner wall and said outer wall, distal ends of said optical fibers in said at least one group being arranged in a spiral pattern extending radially outward from said inner wall to said outer wall, the distal ends of optical fibers in said at least one group being circumferentially spaced from distal ends of optical fibers in any other group.

7. A fiber optic catheter comprising:
an outer cylindrical wall;
an inner cylindrical wall;
at least one group of a plurality of optical fibers disposed between said inner wall and said outer wall, distal ends of said optical fibers in each group being arranged on a radially straight line extending from said inner wall to said outer wall, the distal ends of optical fibers in said at least one group being circumferentially spaced from distal ends of optical fibers in any other group.

8. A method for ablating a target in a lumen using a fiber optic catheter, comprising the steps of:
inserting said catheter into said lumen, said catheter having:
an outer cylindrical wall, and
a plurality of spaced groups of optical fibers disposed within said outer wall, a sum of cross-sectional areas of said optical fibers at a distal end of said catheter being substantially less than a cross-sectional area of said catheter, said fibers of each spaced group being arranged at said distal end to sweep an area substantially equivalent to an area of said distal end of said catheter when said catheter is rotated;
positioning said catheter so that said optical fibers are aimed at a target;
emitting energy through said optical fibers at the target; and
at the same time as said emitting step, rotating the catheter such that beams from said fibers sweep out circular paths covering substantially the entire area of the extreme distal end of said catheter so that the target is ablated.

9. A method as in claim 8, wherein said distal ends of at least one group of said optical fibers are arranged along a radius of said catheter so that said emitting step causes radiation to be emitted in a straight wall from said at least one group.

10. A method as in claim 8, wherein said distal ends of at least one group of said optical fibers are arranged spirally so that said emitting step causes radiation to be emitted in a curved wall from said at least one group.

11. A method for ablating a target in a lumen using a fiber optic catheter, comprising the steps of:
inserting said catheter into said lumen, said catheter having:
an outer cylindrical wall,
an inner cylindrical wall within said outer wall, and
at least one group of a plurality of optical fibers disposed between said inner wall and said outer wall, distal ends of said optical fibers in said at least one group being arranged in a spiral pattern extending radially outward from said inner wall to said outer wall, the distal ends of optical fibers in said at least one group being circumferentially spaced from distal ends of optical fibers in any other groups;
positioning said catheter so that said optical fibers are aimed at a target;
emitting energy through said optical fibers at the target; and
at the same time as said emitting step, rotating the catheter such that beams from said fibers sweep out circular paths of difference radii covering substantially the entire area of the extreme distal end of said catheter so that the target is ablated.

12. A method for ablating a target in a lumen using a fiber optic catheter, comprising:
inserting said catheter into said lumen, said catheter having;
an outer cylindrical wall,
an inner cylindrical wall within said outer wall, and
at least one group of a plurality of optical fibers disposed between said inner wall and said outer wall, distal ends of said optical fibers in said at least one group being arranged on a radially straight line extending from said inner wall to said outer wall, the distal ends of optical fibers in said at least one group being circumferentially spaced from distal ends of optical fibers in any other group; positioning said catheter so that said optical fibers are aimed at a target;
emitting energy through said optical fibers at the target; and
at the same time as said emitting step, rotating the catheter such that beams from the fibers sweep out circular paths of differing radii covering substantially the entire area of the extreme distal end of said catheter so that the target is ablated.

13. A fiber optic catheter comprising;
an outer cylindrical wall;
an inner cylindrical wall within and separated from said outer wall, said inner cylindrical wall defining an inner lumen therewithin;
a plurality of optical fibers provided in at least one group, a distal end of each optical fiber in said at least one group being radially contiguous with distal ends of adjacent optical fibers in said at least one group, said distal ends of said optical fibers in said at least one group extending from said inner wall to said outer wall, distal ends of optical fibers in said at least one group being circumferentially spaced from distal ends of optical fibers in any other group.

* * * * *